(12) United States Patent
Laboureau et al.

(10) Patent No.: US 9,750,675 B2
(45) Date of Patent: Sep. 5, 2017

(54) USE OF GREEN LIGHT TO ACTIVATE L-AMINO ACID OXIDASE

(75) Inventors: Julien Laboureau, Paris (FR); Quang Lan Nguyen, Antony (FR)

(73) Assignee: L'OREAL, Paris (FR)

( * ) Notice: Subject to any disclaimer, the term of this patent is extended or adjusted under 35 U.S.C. 154(b) by 747 days.

(21) Appl. No.: 12/668,689

(22) PCT Filed: Jul. 16, 2008

(86) PCT No.: PCT/FR2008/051333
§ 371 (c)(1),
(2), (4) Date: May 3, 2010

(87) PCT Pub. No.: WO2009/019381
PCT Pub. Date: Feb. 12, 2009

(65) Prior Publication Data
US 2010/0228181 A1    Sep. 9, 2010

Related U.S. Application Data

(60) Provisional application No. 60/982,455, filed on Oct. 25, 2007.

(30) Foreign Application Priority Data

Jul. 16, 2007   (FR) ..................... 07 56506

(51) Int. Cl.
| | |
|---|---|
| A61K 8/44 | (2006.01) |
| A61K 8/49 | (2006.01) |
| A61K 8/67 | (2006.01) |
| A61Q 19/08 | (2006.01) |
| A61N 5/06 | (2006.01) |
| A61N 5/067 | (2006.01) |

(52) U.S. Cl.
CPC .............. *A61K 8/44* (2013.01); *A61K 8/442* (2013.01); *A61K 8/447* (2013.01); *A61K 8/4953* (2013.01); *A61K 8/4973* (2013.01); *A61K 8/673* (2013.01); *A61N 5/0616* (2013.01); *A61Q 19/08* (2013.01); *A61K 2800/78* (2013.01); *A61K 2800/81* (2013.01); *A61N 5/0617* (2013.01); *A61N 2005/067* (2013.01); *A61N 2005/0652* (2013.01); *A61N 2005/0654* (2013.01)

(58) Field of Classification Search
CPC ........ A61K 8/44; A61K 8/4953; A61K 8/673; A61K 8/442; A61K 8/4973; A61K 8/447; A61K 2800/78; A61K 2800/81; A61Q 19/08; A61N 2005/0652; A61N 5/0616; A61N 5/0617; A61N 2005/067; A61N 2005/0654

See application file for complete search history.

(56) References Cited

U.S. PATENT DOCUMENTS

| | | | |
|---|---|---|---|
| 4,197,316 A | | 4/1980 | Yu et al. |
| 4,234,691 A | * | 11/1980 | Kusakabe et al. ............ 435/191 |
| 4,357,425 A | * | 11/1982 | Yoshino et al. ............... 435/191 |
| 4,614,714 A | * | 9/1986 | Kusakabe et al. ............. 435/25 |
| 5,061,480 A | | 10/1991 | Marchese et al. |
| 5,091,171 A | * | 2/1992 | Yu et al. ........................ 424/642 |
| 6,645,230 B2 | * | 11/2003 | Whitehurst .................... 607/88 |
| 2003/0095959 A1 | * | 5/2003 | Mayne ......................... 424/94.4 |
| 2004/0247686 A1 | | 12/2004 | Okada et al. |
| 2006/0275243 A1 | | 12/2006 | Blume et al. |
| 2007/0255355 A1 | * | 11/2007 | Altshuler ............. A61B 18/203 607/86 |

FOREIGN PATENT DOCUMENTS

| | | | |
|---|---|---|---|
| DE | 1980222 A1 * | 7/1998 | ............... A61N 5/06 |
| EP | 1 637 123 | 3/2006 | |
| EP | 1 726 296 | 11/2006 | |
| FR | 2 729 076 | 7/1996 | |
| FR | 2 895 680 | 7/2007 | |
| JP | 60-87786 A | 5/1985 | |
| JP | 2002-293731 A | 10/2002 | |
| JP | 2005-125075 A | 5/2005 | |
| JP | 2006-525950 A | 11/2006 | |
| WO | WO 9425574 A1 * | 11/1994 | ............... C12N 9/06 |
| WO | 2004 087167 | 10/2004 | |

OTHER PUBLICATIONS

L-amino acid oxidase. Product Information from Sigma; A-9253. Feb. 2001. p. 1.*

Macheroux et al. L-Amino-acid oxidase from the Malayan pit viper *Calloselasma rhodostoma*. Eur. J. Biochem. 268, 1679-1686 (2001).*

Mitra et al. Irreversible inactivation of snake venom l-amino acid oxidase by covalent modification during catalysis of L-propargylglycine. FEBS Open Bio 3 (2013) 135-143.*

(Continued)

*Primary Examiner* — Taeyoon Kim
(74) *Attorney, Agent, or Firm* — Oblon, McClelland, Maier & Neustadt, L.L.P.

(57) ABSTRACT

The present invention relates to the use of a source of green light for activating L-amino acid oxidase in the presence of at least one substrate of this enzyme in order to stimulate the energy metabolism of the cells of the skin, to stimulate their replacement and thus to improve the appearance of the skin and hair, in particular to prevent and/or treat cutaneous signs of ageing of the skin and hair.

8 Claims, 2 Drawing Sheets

(56) References Cited

OTHER PUBLICATIONS

Vinck et al. Green Light Emitting Diode Irradiation Enhances Fibroblast Growth Impaired by High Glucose Level. Photomedicine and Laser Surgery.vol. 23, No. 2, 2005. p. 167-171.*
MEM from Life Technology. Downloaded from www.invitrogen.com/site/us/en/home/support/Product-Technical-Resources/media_formulation.92.html on Aug. 19, 2013. p. 1-2.*
Gazzola et al. The Transport of Neutral Amino Acids in Cultured Human Fibroblasts. The Journal of Biological Chemistry vol. 255. No. 3, Issue of Feb. IO, pp. 929-936. 1980.*
Office Action as received in the corresponding Japanese Patent Application No. 2010-516556 dated Feb. 10, 2014 w/English Translation.
Office Action issued Mar. 30, 2015 in Japanese Patent Application No. 2010-516556 (submitting English translation only).
Japanese Office Action issued Oct. 31, 2016 in Patent Application No. 2015-14330 (without English translation).

* cited by examiner

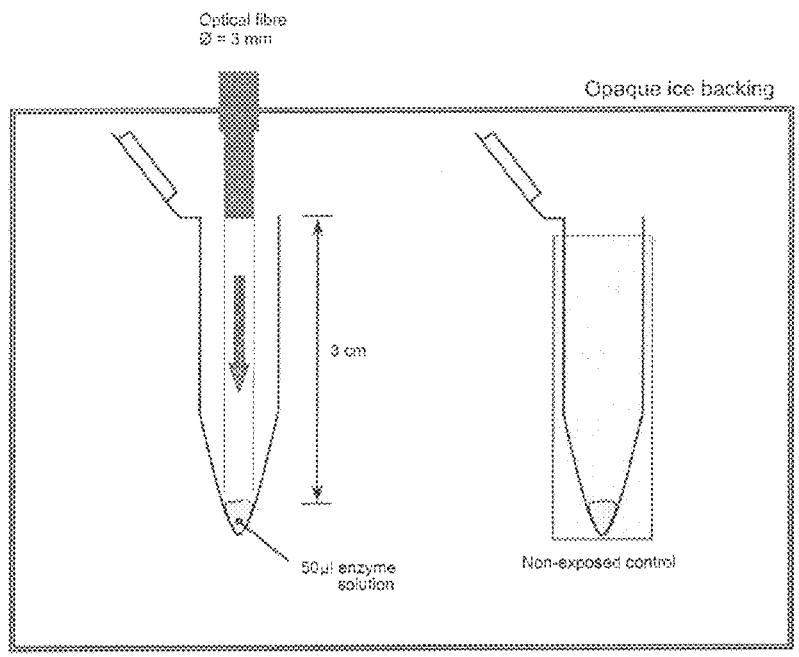
Figure 1 – Assembly diagram allowing to expose enzyme to green light between 500-560 nm
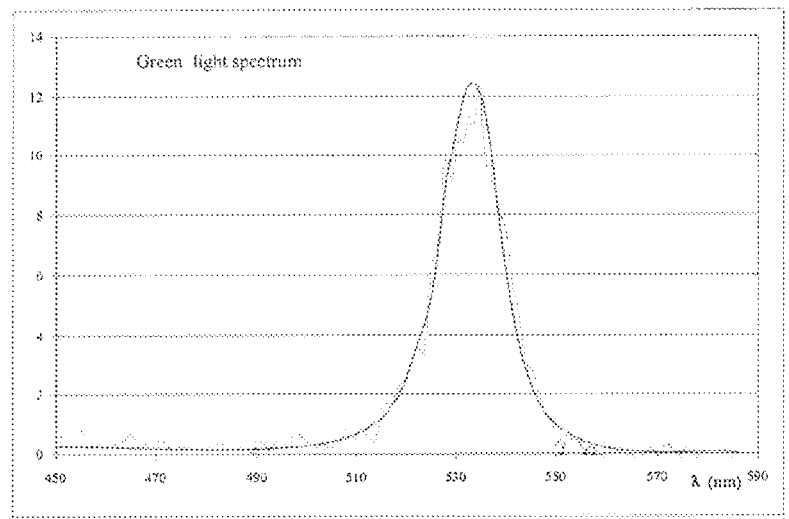
Figure 2 – Characteristics of the light used in the tests

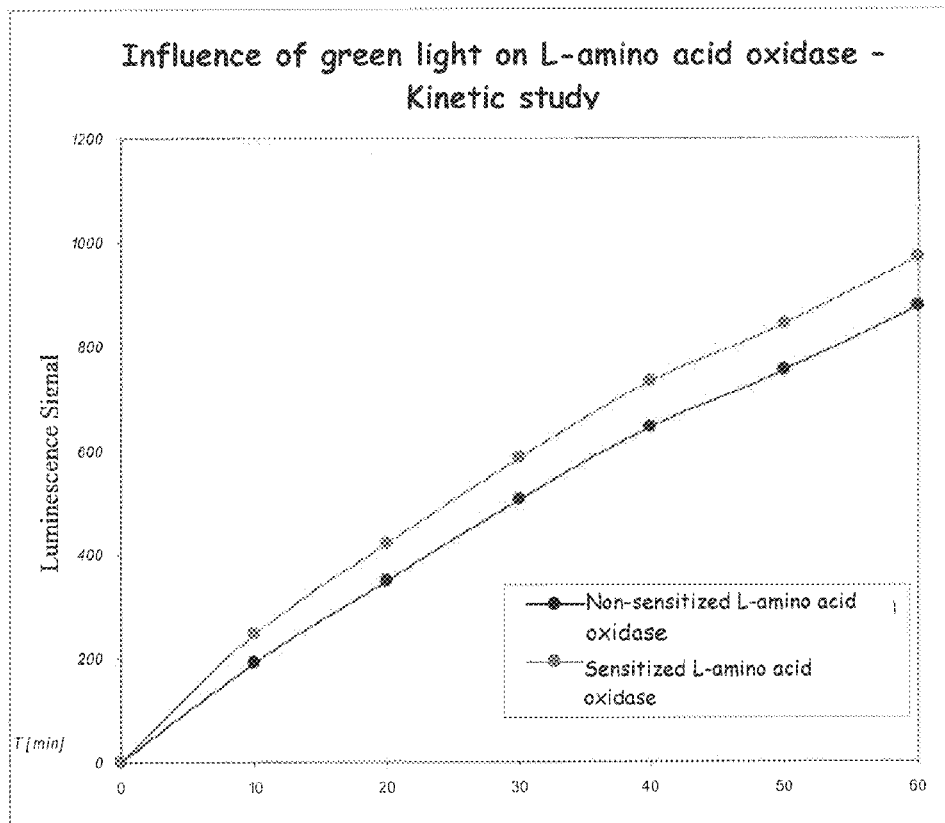
Figure 3 : results of example 2
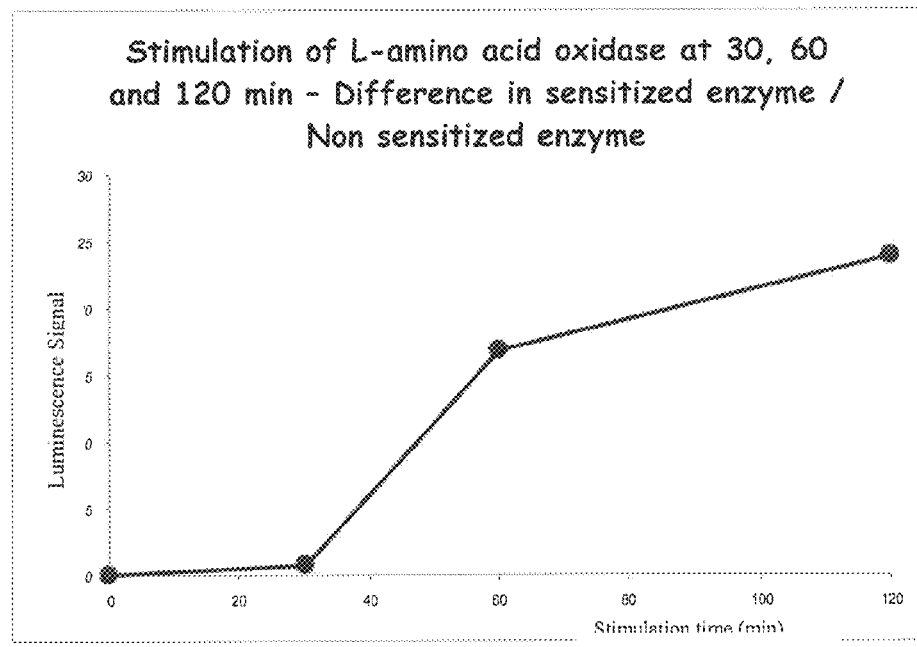
Figure 4 : results of example 3

USE OF GREEN LIGHT TO ACTIVATE L-AMINO ACID OXIDASE

CROSS-REFERENCE TO RELATED APPLICATIONS

This application is a National Stage of PCT/FR08/051333 filed Jul. 16, 2008 and claims the benefit of FR 07 56506 filed Jul. 16, 2007.

FIELD OF THE INVENTION

The present invention relates to the field of the care of the skin and hair and in particular of the improving of the physiological balance of the skin and hair and the prevention and/or treatment of their ageing.

The present invention relates more specifically to the use of a source of green light for activating L-amino acid oxidase in the presence of at least one substrate of this enzyme in order to stimulate the energy metabolism of the cells of the skin, to stimulate their replacement and thus to improve the appearance of the skin and hair, in particular to prevent and/or treat cutaneous signs of ageing of the skin and hair.

The invention also relates to a composition comprising at least one substrate of the enzyme and at least one substrate capable of emitting green light, to a kit comprising a green light device and the composition comprising at least one substrate of the said enzyme and to a cosmetic method employing the compositions or kits according to the invention.

BACKGROUND OF THE INVENTION

The skin is an external organ of the body constantly subjected to attacks from the external environment, such as solar radiation, atmospheric pollutants, and the like.

These external factors, but also the gradual decline in the various functions of the body during ageing, contribute to an accumulation of damaged cell components (nucleic acids, lipids, proteins), the removal and/or the repair of which should be carried out by the cell.

The formation of damaged cell components takes place mainly via reactions involving reactive oxygen entities, such as the superoxide anion, hydrogen peroxide or the hydroxyl radical. Other reactions involving the attachment to macromolecules of glucosides or aldehydes resulting from lipid peroxidation also contribute thereto (Friguet B. Le vieillissement moléculaire et cellulaire et ses futures enjeux [Molecular and Cell Ageing and its Future Challenges], Mécanismes biochimiques).

BRIEF SUMMARY OF THE INVENTION

The aim of retaining a youthful appearance and/or a healthy skin results in the ceaseless search for novel compounds and/or novel compositions which make it possible to maintain and/or improve the appearance of the skin.

This has been achieved by the Applicant Company by combining the application of composition comprising at least one substrate of L-amino acid oxidase and the exposure to a green light which has the effect of activating the enzyme L-amino acid oxidase.

BRIEF DESCRIPTION OF THE DRAWINGS

FIG. 1 shows an assembly diagram allowing to expose enzyme to green light between 500 and 560 nm.

FIG. 2 shows characteristics of the light used in the Examples.

FIG. 3 shows the results of Example 2.

FIG. 4 shows the results of Example. 3

DETAILED DESCRIPTION OF THE INVENTION

It is known to use light rays for the treatment of the skin. Mention may be made, as such, of:

laser beams, which are electromagnetic radiation with a wavelength of 532 nm which are used in particular to treat the phenomena of telangiactasia or age-related hyperpigmentation (Robert et al., 2003). Several studies have shown that laser beams emitted at the wavelength of 1064 mm improve cutaneous regeneration. The laser beams applied in pulsed fashion at 585-595 nm markedly improve wrinkles located in the periorbital region.

IPL (Intense Pulsed Light): electromagnetic radiation with a broad spectrum between 500 and 1200 nm (IPL) has been widely described for improving phenomena of ageing. The use of specific filters makes it possible to isolate wavelengths and to retain only the electromagnetic radiation suited to the types of treatments desired. It has been shown that the simultaneous emission of yellow, red and infrared radiation makes it possible to regulate several different biological activities and thus to regulate various detrimental changes related to photoageing.

Infrared radiation: several studies have shown the effect of broad-spectrum infrared irradiation on the biology of the skin. In particular, it has been described that the absorption of infrared radiation by water molecules of the tissue causes a localized increase in heat in the dermis, resulting in an increase in the synthesis of matrix molecules and in particular of collagen. More recently, it has been shown that irradiation with infrared radiation protects the fibroblasts of the dermis from the harmful effect of irradiation with UV radiation. In these studies, the authors show that this protection involves the regulation of a mitochondrial protein, cytochrome C (Menezes et al., 1998).

More and more scientific teams are trying to determine the mechanism of biological action of the LED. It has been shown in particular that the LED, by targeting photoreceptors (chromophores), activates the oxidation-reduction sequence located in the mitochondrial membrane. This stimulation would then result, in the fibroblasts, in the production of fibrillar proteins, collagens and elastin, and in the reduction in the expression of metalloproteinases MMPS (Robert et al., 2003). In a recent study, it had been shown by Vinck et al., 2005, that irradiation with a source of LED at 570 nm results in an increase in the proliferation of fibroblasts.

The Applicant Company has discovered, surprisingly and unexpectedly, that the application to the skin of a substrate of L-amino acid oxidase, accompanied by an emission of green light, results in an increased activity of this enzyme and exhibits advantageous effects on the stimulation and regulation of the physiological activity of the skin.

L-Amino acid oxidase (EC 1.4.3.2) belongs to the family of the amino acid oxidases.

Amino acid oxidase enzymes are present in the various cell types of the skin.

They catalyse the conversion of the amine functional groups to ketone functional groups. The conversion of an amino acid by these enzymes thus gives rise to the corresponding keto acid compound.

The Application Company has now demonstrated that green light has the property of increasing the activity of L-amino acid oxidase.

Amino acids are fuels which, after conversion in the cytoplasm of the cell, enter the mitochondria in order to be decomposed therein.

Alanine, in particular, can directly give rise to the pyruvate by catalytic oxidative deamination with L-amino acid oxidase.

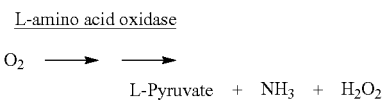

$$\text{L-alanine} + H_2O + O_2 \xrightarrow{\text{L-amino acid oxidase}} \text{L-Pyruvate} + NH_3 + H_2O_2$$

In the mitochrondria, the pyruvate is converted to ATP, the main energy source of the cell.

Keto acid compounds include in particular pyruvate or also acetoacetate.

The formation of acetoacetate can also be induced by oxidative deamination according to the same principle as that mentioned above starting from the aminobutyrate.

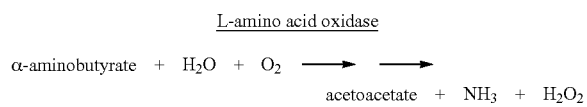

$$\alpha\text{-aminobutyrate} + H_2O + O_2 \xrightarrow{\text{L-amino acid oxidase}} \text{acetoacetate} + NH_3 + H_2O_2$$

A subject-matter of the invention is thus the use of green light to activate L-amino acid oxidase in the presence of at least one of its substrates.

Such a use has the effect of increasing the potential for phosphorylation which activates signals resulting in the expression of genes and of activating the metabolism of the cells of the skin, in particular fibroblasts, keratinocytes and melanocytes, of activating and regulating the physiology of these cells, in particular by reducing the formation and by stimulating the removal of damaged cell components, especially components resulting from oxidative stress.

One consequence of this effect is to improve the replacement of the cells of the dermis and eperdermis and thus cutaneous regeneration.

The use according to the invention thus makes it possible to give a healthy appearance to the skin and hair, that is to say to unify the complexion, to rekindle its radiance, to prevent its yellow or lifeless appearance; to prevent and/or treat cutaneous blemishes; to tone down visible and/or tactile irregularities of the surface of the skin, to give it a more uniform relief and to smooth it, to prevent and/or treat wrinkles and fine lines; to restore greater thickness and elasticity to the skin, in particular for regions where the skin is more relaxed, for example on the outline of the face or on the neck.

The use according to the invention also makes it possible to combat detrimental changes to the skin related to ageing, to prevent and/or treat cutaneous signs of ageing of the skin and signs of ageing of the hair; to improve healing.

In particular, the use according to the invention makes it possible to increase the synthesis of matrix macromolecules of the dermis (collagen fibrils, GAG, elastic fibres) and to prevent their decomposition; it also prevents the detrimental change in epidermal homeostasis.

The term "cutaneous signs of ageing of the skin" is understood to mean in particular a relaxing of the skin, the prevention of wrinkles or cutaneous blemishes or a yellowing of the complexion.

The term "signs of ageing of the hair" is understood to mean in particular loss of hair, the slowing of its growth, its greying, the decrease in the diameter of the individual hairs or the decrease in the vigour of the hair.

The use of the invention takes place by the simultaneous or offset administration of a composition comprising at least one substrate of L-amino acid oxidase and green light to the area where the said composition has been applied.

The substrates of L-amino acid oxidase which can be used according to the invention are amino acids or a molecule comprising an amine functional group, the substrate being such that it comprises a carbon in the α position with regard to the acid group and a primary amine group; more particularly, L-amino acids are concerned.

The said substrate is chosen from leucine, serine threonine, glycine, alanine, valine, phenylalanine, tyrosine, lysine, arginine, cysteine, aspartate, glutamate, citrulline, ornithine, diaminopimelic acid, penicillamine or α-aminobutyric acid.

Preferably, the invention is implemented with alanine, glycine, α-aminobutyric acid, lysine, leucine, serine and threonine.

The amino acids can be formulated in the form of salts, such as sodium or alkaline earth metal (for example manganese or calcium) salts.

According to a preferred form, the invention is implemented using a topical composition comprising at least one substrate of L-amino acid oxidase.

The term "topical composition" is understood to mean a composition intended for local application to any surface of the body, including the skin, mucous or semimucous membranes, or scalp.

The compositions of use according to the invention are in particular cosmetic or dermatological compositions.

The composition generally comprises a physiologically acceptable medium, that is to say a medium compatible with the skin and/or its superficial body growths. It is preferably a cosmetically acceptable medium, that is to say a medium which exhibits a pleasant smell, a pleasant colour and a pleasant feel and which does not cause unacceptable discomfort (smarting, red blotches, tightness) liable to dissuade the consumer from using this composition.

The topical composition according to the invention comprises an effective amount of substrate (amino acid) also chosen according to the solubility of the amino acid in the formulation under consideration; this amount of substrate of L-amino acid oxidase is preferably between 0.001 and 10%, more preferably between 0.01 and 1%.

According to the area of the body targeted and the intensity of application desired, a person skilled in the art can choose from different composition forms:

a composition intended to remain applied to the skin even after the exposure to the green light; this composition can be a dispersion of the lotion or gel type, an emulsion with a liquid or semiliquid consistency of the milk type obtained by dispersion of a fatty phase and an aqueous phase (O/W) or vice versa (W/O), or a suspension or emulsion with a soft, semisolid or solid consistency of the cream or gel type, or also multiple (W/O/W or O/W/O) emulsions, a microemulsion, a vesicular dispersion of anionic and/or non-ionic type, or a wax/aqueous phase dispersion;

a composition which remains in contact with the skin only during the period of the exposure to the green light, such as a mask, in the form of a cream which a user can specifically apply to the areas to be treated and can then subsequently remove, or a patch impregnated with a substrate; in this administration form, the masks or patches must be sufficiently transparent to allow the green light to pass through.

In the context of the present invention, any source of green-coloured light emitting at a wavelength such that it activates L-amino acid oxidase, which can be between 500 and 580 nm, preferably between 500 and 560 nm.

Mention may in particular be made of:

lasers (for light amplification by the stimulated emission of radiation); these are monochromatic light sources of very high intensity.

Unlike white light (photons of various wavelengths emitted in random fashion at different times and in different directions), the light radiation emitted by a laser is a light composed of photons emitted at the same time and in the same direction.

Three elements characterize laser beams: the wavelength ($\lambda$); the mode of emission: continuous (constant power delivered), pulsed (energy is delivered via pulses, the frequency and the power of which can be adjusted) and ultrapulsed (the pulses have a fixed duration and a fixed power and the power is high and the duration extremely short); and the power: from a few mW to tens of thousands of watts.

IPL: Intense Pulsed Light.

The fundamental difference between laser and IPL lies in the fact that IPL can deliver hundreds, indeed even thousands, of colours simultaneously, whereas the laser delivers only a single wavelength. These machines make it possible to choose the wavelength suited to the problem to be treated, just by changing the filter. They are also referred to by the term "non-coherent light source".

It is a matter of emission of pulses of light of high overall intensity.

This technology can deliver a broad spectrum of wavelengths which are absorbed by multiple chromophores. Large surface areas can be treated simultaneously.

LEDs: Light-emitting diode (photomodulation (LED, Light Emitting Diode, see "The newest Medical breakthrough for skin renewal and Shrinking pores (2004) ")).

The LED: the LED generally emits light at low intensity of a few milliwatts and at a wavelength of 590+/−10 to 20 nm; they are classified in the category of low-power lasers (1 to a few tens of mW).

The present invention can also be implemented using substances which emit green light.

These substances are more particularly metabolites or active principles which emit light between 500 and 580 nm on exposure to UV radiation, for example vitamin B2, which decomposes to give lumiflavine which fluoresces in the green, baicailine in acid medium, fisetin, dipyridamole, green phosphorescent pigments or minerals. They are chosen in particular from lumiflavine, baicailine in acid medium, fisetin, dipyridamole, green phosphorescent pigments and minerals.

These sources of green light are used in an amount or intensity sufficient to provide a light emission flux from 1 to a few tens of mV.

A person skilled in the art will adjust the exposure time to green light according to the characteristics of the light source and the effect desired; purely by way of indication, the cutaneous regions to be treated can receive a light power of at least 500 to 1500 mJ/cm$^2$ and preferably of between 500 and 90 000 mJ/cm$^2$.

The source of green lights can also be a green phosphorescent or fluorescent substance.

The term "green phosphorescent pigments" is understood to mean the conventional phosphorescent pigments listed below but also any cosmetically acceptable substance which emits a green phosphorescent light with a wavelength of between approximately 500 and 580 nm.

The presence of phosphorescent pigments provides the composition with a continuous source of green light; the phosphorescence is activated by the exposure to UV radiation conventionally present in daylight and its effect lasts several hours.

Various compounds are known for having the property of phosphorescing in the green, comprising, without limitation:
zinc sulphide (doped with copper and/or manganese),
strontium aluminates,
phosphorescent calcite,
ceramic oxides doped with rare earth metal elements, such as yttrium doped with Al, gallium, terbium doped with Sr or dysprosium ($Y_3$ (Al,Ga)$SO_2$, $Y_2SiO_5$, $SrGa_2S_4$: Eu),
zinc borosilicates (glass) doped with copper or rare earth metal elements,
rare earth metal oxides.

Light sources which are fluorescent in the green can be used to supplement or replace phosphorescent light sources.

The preferred sources of green fluorescent light are fluorescent minerals.

Mention may be made, by way of example and without a limiting nature, of: andalusite and chiastolite (aluminium silicate); amblygonite (basic lithium aluminium phosphate); phenakite (beryllium silicate); variscite (hydrated aluminium phosphate); serpentine (basic magnesium silicate); amazonite (potassium aluminium silicate); amethyst (silicon dioxide); chrysoberyl (beryllium aluminium oxide); turquoise (basic aluminium phosphate comprising copper); colourless, yellow or pink tourmaline (borosilicate); amber (succinite/resins); opal (hydrated silicon dioxide); cerussite (lead carbonate); fuchsite (potassium aluminium silicate); diopside (calcium magnesium silicate); ulexite (hydrated sodium calcium borate); aragonite (calcium carbonate); and willemite (zinc silicate).

Mention may also be made of the lattices of polymers which act as prisms and have the property, on choosing the appropriate refractive index, of emitting green light when they are illuminated with white light.

It is also possible to promote the access of green light to the skin by applying green coloured compositions which have the role of screening the light in order to allow only the green light to pass, such as chromium oxides, chlorophyll, kermaline, tourmaline, powders formed from green precious and semiprecious stones (emerald, and the like).

These substances can be used at concentrations sufficient to ensure the passage of an amount of green light capable of activating L-amino acid oxidase, for example of between 0.01% and 20%.

A further subject-matter of the invention is a composition comprising at least one substrate of L-amino acid oxidase and at least one compound chosen from active principles which emit light between 500 and 580 nm on exposure to UV radiation, green phosphorescent substances, green fluorescent substances and substances which screen light in order to allow only green light to pass through; these compounds are as described above.

Preferably, it concerns a topical composition as described above.

The invention also relates to a composition in the form of a combination product, for a use which is simultaneous, separate or spread out over time, comprising at least one substrate of L-amino acid oxidase as described above and at least one compound chosen from active principles which emit light between 500 and 580 nm on exposure to UV radiation, green phosphorescent substances, green fluorescent substances and substances which screen light in order to allow only green light to pass through; preferably, the active principle which emits light on exposure to UV radiation is chosen from lumiflavine, baicailine in acid medium, fisetin, dipyridamole, green phosphorescent pigments or minerals.

The compositions and methods according to the invention make it possible to solve the potential problems of harmlessness and of formulation brought about by the use of enzymes, the activity of which must not be detrimentally affected by the formulation.

Another subject-matter of the invention is a cosmetic method for improving the appearance of the skin, improving the radiance of the complexion, toning down visible or tactile irregularities of the surface of the skin, in particular for toning down wrinkles and fine lines and/or cutaneous blemishes, and/or smoothing the skin and/or lightening the complexion, comprising the topical application of a composition comprising at least one substrate of L-amino acid oxidase and the exposure of the region on which the said composition has been applied to green light with a wavelength of between 500 and 580 nm.

Another subject-matter of the invention is a cosmetic method for combating ageing of the hair, the slowing of its growth, its greying, the reduction in the diameter of the individual hairs or the reduction in the vigour of the hair, comprising the topical application of a composition comprising at least one substrate of L-amino acid oxidase and the exposure of the region on which the said composition has been applied to a green light with a wavelength of between 500 and 580 nm.

For the implementation of the methods according to the invention, the source of green light is chosen from lasers, IPL, LEDs, metabolites or active principles which emit light between 500 and 580 nm on exposure to UV radiation, green phosphorescent substances or green fluorescent substances.

The method according to the invention will also be able to comprise a stage of exposure to UV radiation.

According to another of its subject-matters, the present invention relates to a kit comprising:
a. a composition comprising at least one substrate of an enzyme, L-amino acid oxidase, the activity of which can be increased by a green light emission;
b. a source of green light.

The implementation of the method can consist in carrying out stages a and b simultaneously, separately or else offset in time.

In particular, the said substrate of L-amino acid oxidase is chosen from leucine, serine, threonine, glycine, alanine, valine, phenylalanine, tyrosine, lysine, arginine, cysteine, aspartate, glutamate, citrulline, ornithine, diaminopimelic acid, penicillamine or α-aminobutyric acid.

The said composition corresponds to the technical characteristics described above.

The source of green light is chosen from lasers, IPL, LEDs, metabolites or active principles which emit light between 500 and 580 nm on exposure to UV radiation, green phosphorescent substances or green fluorescent substances.

Thus, according to a specific embodiment of the kit, the source of green light is a substance which emits green light formulated in the composition comprising the said substrate of L-amino acid oxidase or else in another topical composition intended to be applied in an offset fashion (before or after).

The kit can also be employed using a patch, in particular an iontophoretic patch, impregnated with at least one substrate of L-amino acid oxidase and provided with diodes emitting a green light.

The implementation of the method according to the invention can additionally comprise a stage, prior to or concomitant with stages a and/or b, of treatment of the skin targeted at improving the penetration of the substrate, for example by cooling the skin, by iontophoresis, by an occlusive system.

It is also possible to promote the penetration of the substrate by carrying out a preliminary chemical or mechanical peeling on the area to be treated.

Example 1—Activation of L-Amino Acid Oxidase with Green Light

The following example measures the stimulating effect of green light (500-560 nm) on the activity of the enzymatic chromophore, L-amino acid oxidase. The exposure of its enzyme to green light stimulates the conversion of the amino acids to keto acids.

Description of the Protocol

General principle: the principle of these studies is to compare the activity of amino acid oxidase with or without preliminary exposure to a source of light between 500-560 nm.

Equipment and Reactants

Source, with optical fibre (the internal diameter 3 mm)
Photometre IL-1700+SED 033 probe (#6600),
L-amino acid oxidase: Sigma, ref. A-9253 (batch 064K0773) at 0.39 units/mg solid,
D-amino acid oxidase: Sigma, ref. A-5222-100UN (batch 115K1101) at 2.3 units/mg solid.

Mode of Exposure of the Enzymes

The enzyme (dehydrated powder form or enzyme solution) is placed in a conical Eppendorf tube. The amount is adjusted so that the enzymes in their entirety are subjected to exposure to light (wavelengths of between 490 and 585 nm) by an optical fibre with a diameter of 3 mm. Exposure to light is continuous and the energy provided by the light is 0.45 mW/cm$^2$ (see FIG. 1: assembly diagram, and FIG. 2: characteristics of the light used in the tests).

The Eppendorf tubes are placed in an ice bath throughout the duration of the exposure in order to avoid an effect of the temperature. The control enzyme (not exposed to light between 500-560 nm) is prepared at the same time and in the same way and is protected from the light by a backing which prevents the external light from arriving (aluminium paper).

Measurement of Activity of the Enzyme

The activity of the enzyme is measured by chemiluminescence.

The substrate of the enzyme (L-leucine and/or D-alanine) is incubated for different times with amino acid oxidase in a specific buffered medium. The formation of the hydrolysis product $H_2O_2$ is monitored by chemiluminescence in the presence of peroxidase and isoluminol according to the protocol for the quantitative determination of the activity of these enzyme (E.C. 1.4.3.2) described in "The Worthington Manual", Enzymes and Related Biochemicals, Editor: Charles C. Worthington, 1988, pages 35-37). The hydrolysis product $H_2O_2$ which results therefrom is quantitatively determined by chemiluminescence with the presence of peroxidase and isoluminol reaction mixture prepared as follows:

Chemiluminescence Reaction Mixture:

34.8 mg of isoluminol are weighed out and dissolved with magnetic stirring in approximately 50 ml of 100 mM borate buffer. 2 mg of microperoxidase are weighed out and dissolved with magnetic stirring in approximately 5 ml of 100 mM borate buffer. The two reactants are then mixed in a 200 ml volumetric flask, the volume of which is adjusted with borate buffer (each beaker is rinsed 3 times with buffer). The 200 ml are placed in a 500 ml flask. 200 ml of borate buffer are then again added thereto. The reaction mixture, the final volume of which is 400 ml, is homogenized by magnetic stirring and then placed in darkness at ambient temperature at least 24 hours before use.

The luminescence is read using the "Fluoroskan Ascent FL" luminometer from Thermo Labsystems.

Results: Specific Enzymatic Activation of L-Amino Acid Oxidase

Influence of the green light on D-amino acid oxidase.
D-Amino Acid Oxidase

| Condition | Control | Green light |
|---|---|---|
| Luminescence | 577.5 | 568.2166667 |

Influence of the green light on L-amino acid oxidase.
L-Amino Acid Oxidase

| Condition | Control | Green light |
|---|---|---|
| Luminescence | 342.26667 | 409.8777778 |

Conclusion

Prolonged exposure to green light does not significantly modify the activity of D-amino acid oxidase. On the other hand, it is observed that an exposure of 60 minutes results in a specific activation of L-amino acid oxidase.

Example 2—Kinetics of Activation of L-Amino Acid Oxidase

Several measurements are carried out after different exposure times according to the protocol described in Example 1 and are summarized in the following table:

The results appear in the table below and are represented in FIG. 3 (the sensitized L-amino acid oxidase is that exposed to green light).

| Anal. time | Control | Green light |
|---|---|---|
| 0 | 0 | 0.0 |
| 10 | 191.56667 | 248.0 |
| 20 | 349.66667 | 420.8 |
| 30 | 502.6 | 586.5 |
| 40 | 646.46667 | 735.2 |
| 50 | 756.26667 | 844.0 |
| 60 | 876.36667 | 970.9 |

Conclusion

The kinetics of activation of L-amino acid oxidase are increased by exposure to light between 500-560 nm.

Example 3—Activation of L-Amino Acid Oxidase According to the Exposure Time: Dose/Response Effect The test is carried out under the same experimental conditions as Example 1 while following the protocol of the supplier.

The results appear in the table below and are represented in FIG. 4.

| Stimulation time | Control | Green light | Difference |
|---|---|---|---|
| 0 | 0 | 0.0 | 0 |
| 30 | 409.9 | 412.8 | 0.7 |
| 60 | 349.7 | 420.8 | 16.9 |
| 120 | 275.4 | 361.7 | 23.8 |

Conclusion

It is found that the longer the exposure to the enzyme, the greater its activity. The following diagram shows the ratio of the activity of the exposed enzyme to that of the control enzyme.

Example 4—Compositions

| Epidermal regeneration cream (oil-in-water emulsion) | |
|---|---|
| Ammonium Polyacryldimethyltauramide (Hostacerin AMPS from Clariant) | 1.00% |
| Cyclohexasiloxane | 5.0% |
| Glycerol | 1.70% |
| Stearyl alcohol | 0.30% |
| Glyceryl stearate/PEG-100 stearate | 0.70% |
| Dimyristyl tartrate/cetearyl alcohol/C12-15 pareth-7/PPG-25 laureth 25 | 0.50% |
| Xanthan gum | 0.20% |
| L-Alanine | 0.5% |
| Preservatives | 0.50% |
| Water | q.s. for 100 |
| Ammonium Polyacryldimethyltauramide (Hostacerin AMPS from Clariant) | 1.00% |
| Cyclohexasiloxane | 5.0% |
| Glycerol | 1.70% |
| Stearyl alcohol | 0.30% |
| Glyceryl stearate/PEG-100 stearate | 0.70% |
| Dimyristyl tartrate/cetearyl alcohol/C12-15 pareth-7/PPG-25 laureth-25 | 0.50% |
| Xanthan gum | 0.20% |
| L-Leucine | 0.5% |
| Preservatives | 0.50% |
| Water | q.s. for 100 |

These creams are applied to the face and/or to the body immediately before prolonged exposure (30 mm to 1 h 30) under radiation with a wavelength of between 500 and 560 nm.

Iontophoretic Patch

A commercial reference patch Iontopatch™ (Travanti Pharma, Mendota Heights, Minn., USA) is applied to a region treated beforehand with one of the above creams.

It is subsequently connected to an electric current in order to deliver a galvanic current generated by a difference in potential of 1 V and comprising two electrodes, a Zn anode and a AgCl cathode, and is exposed under a source of green light.

This treatment is carried out at the rate of once daily for 30 to 45 minutes.

Green Mask

Oily Phase:

| | |
|---|---|
| Octyldodecanol | 6% |
| Apricot kernel oil | 6% |
| Triglycerides | 5% |
| Kaolin | 3% |
| Cetyl alcohol | 2% |
| Vitamin E acetate | 0.5% |
| Hydrogenated palm oil | 6% |
| Liquid fraction of shea butter | 5% |

Aqueous Phase:

| | |
|---|---|
| Xanthan gum | 0.4% |
| Sucrose cocoate/sorbitan stearate (mixture sold by ICL under the name Arlaton 21121) | 5.5% |
| Glycerol | 3% |
| Dipyridamole | 0.30% |
| Copper chlorophyllin | 0.20% |
| Ethanol | 5% |
| L-Alanine | 0.5% |
| Fragrance | 0.3% |
| Preservative | q.s. |
| Water | q.s. for 100 |

This mask is applied to the regions of the skin to be treated and then the subject is placed under a source of white light (natural or electric) for 45 minutes to 1 hour.

The invention claimed is:

1. A method, comprising:
   contacting a surface of skin of a subject with a composition consisting of one or more of ammonium polyacryldimethyltauramide, cyclohexasiloxane, glycerol, stearyl alcohol, glyceryl stearate/PEG-100 stearate, dimyristyl tartrate/cetearyl alcohol/C12-15 pareth-7/PPG-25 laureth 25, xanthan gum, a preservative, and water; and at least one substrate selected from the group consisting of leucine, serine, threonine, glycine, alanine, valine, phenylalanine, tyrosine, lysine, arginine, cysteine, aspartate, glutamate, citrulline, ornithine, diaminopimelic acid, penicillamine and α-aminobutyric acid, wherein the skin comprises L-amino acid oxidase EC 1.4.3.2; and
   activating the L-amino acid oxidase in the presence of the at least one substrate by exposing the surface of skin with green light having a wavelength of from 500 to 580 nm,
   wherein the exposure to green light is obtained from a source selected from the group consisting of a laser, an IPL, and a metabolite or an active principle that emits light between 500 and 580 nm on exposure to UV radiation.

2. The method according to claim 1, wherein a concentration of the at least one substrate in the composition is from 0.001 to 10 weight percent.

3. The method according to claim 1, wherein the composition is a topical composition.

4. The method according to claim 1, wherein the source is a metabolite or active principle that emit light between 500 and 580 nm on exposure to UV radiation and is selected from the group consisting of vitamin B2, baicailine in acid medium, fisetin, dipyridamole, a pigment and a mineral.

5. The method according to claim 1, wherein the source of green light provides light power in a range of from 500 to 90,000 mJ/cm$^2$.

6. The method according to claim 1, wherein the substrate is alanine, leucine or a combination thereof.

7. The method according to claim 6, wherein the substrate is leucine.

8. The method according to claim 6, wherein the substrate is alanine.

* * * * *